(12) United States Patent
Ellman et al.

(10) Patent No.: US 6,562,036 B1
(45) Date of Patent: May 13, 2003

(54) ELECTROSURGICAL ELECTRODE FOR RHINOPLASTY

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 10/006,433

(22) Filed: Dec. 10, 2001

(51) Int. Cl.[7] ............................................. A61B 18/18
(52) U.S. Cl. .......................................... 606/45; 606/41
(58) Field of Search ............................. 606/41, 45, 46, 606/49; 607/101, 115

(56) References Cited

U.S. PATENT DOCUMENTS

| | | | | |
|---|---|---|---|---|
| 5,324,288 A | * | 6/1994 | Billings et al. | 606/45 |
| 5,423,812 A | * | 6/1995 | Ellman et al. | 606/45 |
| 5,505,728 A | * | 4/1996 | Ellman et al. | 606/39 |
| 5,683,387 A | * | 11/1997 | Garito et al. | 606/45 |
| 5,733,282 A | * | 3/1998 | Ellman et al. | 606/45 |
| 5,741,250 A | * | 4/1998 | Garito et al. | 606/45 |
| 5,746,746 A | * | 5/1998 | Garito et al. | 606/41 |
| 6,109,268 A | * | 8/2000 | Thapliyal et al. | 128/898 |
| 2001/0029372 A1 | * | 10/2001 | Quick | 606/45 |

* cited by examiner

*Primary Examiner*—Michael Peffley

(57) ABSTRACT

A novel electrode for use in an electrosurgical rhinoplasty procedure, comprising a uniquely configured electrode having an angled electrode working end terminating in an active, bare, transversely-extending, electrically-conductive, thin wire segment, preferably straight, whose small width enables easy access to the constricted nasal cavity and which in turn is terminated at opposite ends with protective electrically-insulating-coated segments each adjacent an end of the active thin wire segment. The active thin wire is supported by a Y-shaped or U-shaped support.

14 Claims, 2 Drawing Sheets

ELECTROSURGICAL ELECTRODE FOR RHINOPLASTY

This invention relates to an electrosurgical instrument for facial plastic surgery, in particular, to an electrosurgical electrode for rhinoplasty, a procedure to straighten a congenitally or traumatically deviated nose and septum.

BACKGROUND OF THE INVENTION

To the best of our knowledge, this procedure has only been treated by using a scalpel and scissors. Due to the difficulty of gaining access to the inside of the nose, the use of a scalpel to make the intercartilaginous incisions is cumbersome. Frequently, the presence of excessive bleeding dramatically decreases visibility. Knives and septal scissors are further required to release and sculpt upper lateral cartilages while constantly protecting the overlying skin of the nasal dorsum. It is also recognized that cartilage tissue is typically tougher to remove than soft tissue, which further exacerbates the procedure. The result is that the known procedure is time consuming, inefficient and uncomfortable for the patient.

Typically, the surgeon and surgical staff have a very difficult time viewing the procedure and anatomy through the profuse blood produced by the scalpel and scissors. Maneuvering the instruments, stopping the bleeding, and doing a precise rhinoplasty are extremely difficult. It has been indicated that tolerances of less than 1 mm can have a profound effect on the ultimate surgical outcome. Among the main complications with this popular procedure are: 1) poor cosmetic/functional result; 2) septal perforation; and 3) orbital hemorrhage. Many of these serious complications to the patient are related to visibility of critical nasal anatomy and bleeding from the use of the scalpels and scissors. See "Aesthetic Facial Plastic Surgery", ed. by Romo and Millman, published by Thieme, 2000, Ch. 7, whose contents are herein incorporated by reference.

SUMMARY OF THE INVENTION

An object of the invention is an improved rhinoplasty surgical procedure using a novel electrosurgical instrument.

We have invented novel electrodes for use in an electrosurgical rhinoplasty procedure. This electrosurgical procedure using our novel electrodes enables physicians to offer to patients a procedure that is efficiently performed, easily learned and thus performed at a significantly reduced cost, with less tissue damage compared to procedures done heretofore, and, most important, with improved visibility due to control of the bleeding during the procedure.

The procedure using our novel electrodes is based on performing essentially the same kind of rhinoplasty procedure as was used heretofore but, in accordance with a feature of our invention, the structure of our novel electrosurgical electrodes used to remove nasal cartilage tissue provides not only improved access to the cartilage requiring removal but in addition enables simpler removal of the undesired cartilage, much tougher tissue than soft tissue, without the excessive bleeding that impairs visibility of the surgical site.

A further feature of the electrodes of the invention is their size, angle, insulation, and active micro-thin wire to achieve ideal and easy access into the nose, septum, cartilage upper and lower and inferior turbinate.

In accordance with another feature of our invention, the electrode of the invention is uniquely configured to form an angled electrode working end terminating in an active, bare, transversely-extending, electrically-conductive, thin wire segment, preferably straight, whose width enables easy access to the constricted nasal cavity and controls the width of the cartilage planing treatment, and which in turn is terminated at opposite ends with protective electrically-insulating-coated segments each adjacent an end of the active thin wire segment. When the working active end of the activated electrode is applied to the nasal region to be treated, the bare wire delivers radiofrequency energy to the contacted nasal tissue causing the desired cartilage removal. At the protected ends, the electrically-insulating coating prevents the side supports of the active wire from inadvertently contacting and injuring nasal tissue that should remains undisturbed. The novel design with protected side segments will make removal of tough nasal cartilage easier and safer and with less bleeding. The active wire and its side segments are supported by structure that is completely electrically-insulated to avoid damage to surrounding tissue, and to allow the physician to use these inactive insulated parts to help position and guide the active wire segment, which is the only part capable of removing tissue, during the surgical procedure. In a preferred embodiment, the active-wire-supporting structure is Y-shaped.

In accordance with another feature of our invention, the electrode of the invention is uniquely configured to form an angled electrode with a long U-shaped-supported working end terminating in an active, bare, transversely-extending, electrically-conductive, thin wire segment, preferably straight, whose width enables easy access to the constricted nasal cavity and controls the width of the cartilage planing treatment, and which in turn is terminated at opposite ends with protective electrically-insulating-coated segments each adjacent an end of the active thin wire segment. This electrode is especially useful for reducing nasal humps. Similarly to the other preferred electrode, when the working active end of the activated electrode is applied to the nasal region to be treated, the bare wire delivers radiofrequency energy to the contacted nasal tissue causing the desired cartilage removal. As before, the electrically-insulating coating prevents the side supports of the active wire from inadvertently contacting and injuring nasal tissue that should remains undisturbed.

The electrosurgical procedure has the important advantage of being able to remove tough cartilage tissue with minimum surgeon pressure while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

Employment of the invention allows the surgical staff to carry out this procedure with safety, precision and efficiency thus saving considerable time, substantially reduces the complication rate, as well as greatly increasing the success rate of the surgical intervention.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
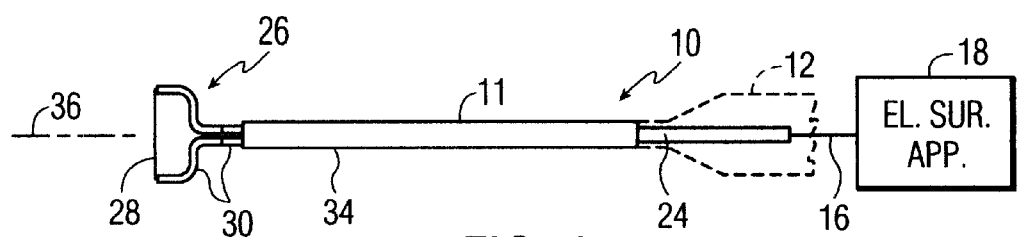
FIG. 1 is a plan top view of one form of electrosurgical instrument in accordance with the invention, shown connected to electrosurgical apparatus.

FIG. 1 illustrates a preferred form of the novel electrosurgical instrument 10 of the invention. It comprises an elongated conventional unipolar handpiece 12 (only the collet end is shown in phantom) of electrically-insulating material having a central electrically-conductive tube or conductor (not shown) extending throughout its length and connected at its end to a cable 16 which is connected in the conventional manner to conventional electrosurgical apparatus 18. As an example only, the electrosurgical apparatus can be model Dual Frequency Surgitron available from Ellman International, Inc. of Hewlett, N.Y. The Ellman equipment is preferred due to its high operating frequency, typically above 2 MHz, preferably above 3 Mhz. This particular apparatus provides unipolar electrosurgical currents at 3.8 MHz.

At the opposite end of the handpiece 12 is mounted one form of the electrosurgical electrode 11 of the invention which comprises an electrically-conductive straight axial brass rod running lengthwise through it and mounted at its shank end 24 nearest the handpiece 12 in the handpiece collet and thus electrically connected to the electrically-conductive cable 16. The distal end of the electrode comprises an electrically-conductive, generally Y-shaped member 26 whose right ends (not shown) are mounted to and electrically connected to the adjacent end of the brass rod. Across the end of the Y-shaped member 26 is a thin straight bare electrically-conducting wire 28, preferably constituted of tungsten wire. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16 and electrically-conductive rod 24 to the tungsten wire 28 serving as the active working end of the electrode. The physician, in the usual way, holds the handpiece 12 while applying the active working end of the electrode to the desired tissue of the patient to be treated.

In accordance with a feature of the invention, the active-wire-supporting Y-shaped member 26 is coated with a thin electrically-insulating coating 30. The brass rod, except for the shank end 24, is also coated with an electrically-insulating coating 34. The active bare thin wire 28 has, for example, a thickness of about 0.005 inches in diameter of tungsten, preferably between about 0.004 and 0.007 inches, and extends generally transverse to an extension of the longitudinal axis 36 of the straight rod 24 of the electrode. The coating 34 for the straight shaft part of the electrode may be one of many suitable electrically-insulating rubber or plastic materials. The coating 30 on the Y-shaped member 26 comprises a thinner coating of an electrically-insulating material, which may be one of many suitable thin electrically-insulating plastics, baked Teflon being one example. Thus, the entire length of the electrode 10 from the bare active wire end 28 to the opposite bare end 24 which is mounted in the handpiece 12 is electrically insulated from the patient. The handpiece 12, too, is completely electrically-insulated. The full length (the vertical dimension in FIG. 1) of the bare wire 28 is exposed. This is a distinguishing feature of one of our earlier issued U.S. Pat. No. 5,746,746, in which the electrically-insulating coating extends around the ends of the Y-shaped member and serves as a spacer to space the active wire from the soft skin tissue being resurfaced. That electrode could not be used for a rhinoplasty procedure because the end electrically-insulating coatings would inhibit access to the nasal tissue, and the lack of a bend in the working end of the electrode (further explained below) would make it extremely difficult to access certain cartilage tissue that needs to be excised in this procedure.

The configuration and dimensions of the electrode of the invention are very important in allowing the surgeon to easily access and remove those nasal tissue regions desired to produce the shape desired. Thus, the length of the active wire 28 in the FIG. 1 embodiment, where the Y-shaped member 26 is angled downwardly, measured transversely to the longitudinal axis 36, is less than about 0.5 inches, preferably about 0.380–0.445 inches, indicated at 40 in FIG. 2; the straight part of the Y-shaped member, indicated at 42 in FIG. 3, is about 0.090–0.099 inches; the angled part, indicated at 44, forms an angle 46 with the horizontal of about 40–50° and comprises a straight part, indicated at 48, of about 0.1–0.2 inches, and a divided part, indicated at 50, of about the same length. The shaft length indicated at 52 is about 1.8 inches, preferably about 1.5–2.0 inches. The shank 24 length, indicated at 53, is about 0.7 inches.

Figure 2:
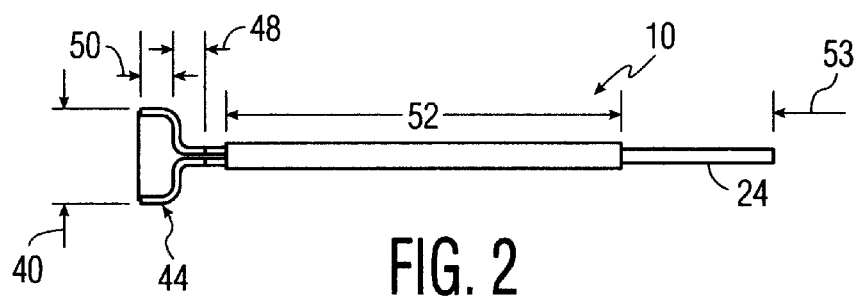
FIG. 2 is a view similar to FIG. 1 for indicating dimensions of the embodiment of the latter.
Figure 3:
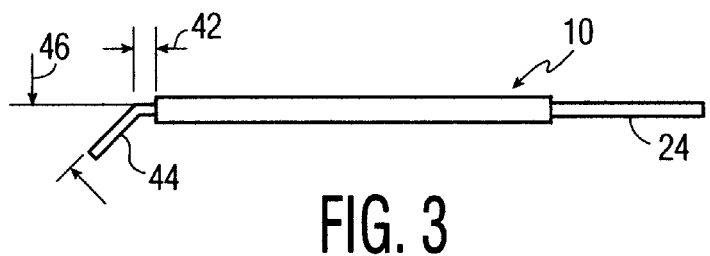
FIG. 3 is a side view of the embodiment of FIG. 1 also indicating some dimensions.
Figure 4:
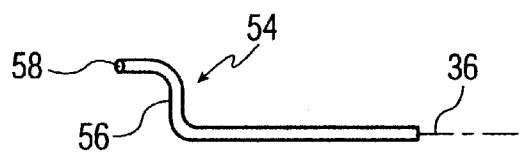
FIG. 4 is a partial view of a variant of an electrosurgical instrument according to the invention.

The preferred embodiment shown in FIGS. 1–3 has a downwardly-angled wire-supporting member 26 which will enable access to many tissue regions within the nasal cavity. However, other tissue regions will not be so easily accessed by that particularly-shaped electrode. Hence, it is desirable to provide a family of electrodes with differently angled ends, differently oriented active wires, and differently-dimensioned parts. For instance, the electrode working end depicted at 54 in FIG. 4 has an upwardly-angled end, indicated at 56, forming an angle of about 80–95° with the horizontal, and terminating in a straight bare wire at its left end perpendicular to the plane of the drawing and visible only as an end dot 58.

Figure 5:
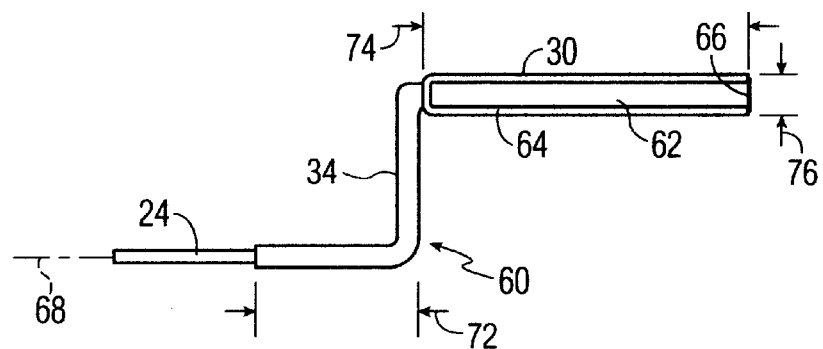
FIG. 5 is a side view of a further variant of an electrosurgical instrument according to the invention.

Another preferred configuration is illustrated in FIG. 5. In this embodiment, starting from the shank end 24 at the left, the shaft part 60 of the electrode is angled upwardly, at an angle of about 80–95° with the horizontal, and terminates in a long U-shaped part 62, corresponding to the Y-shaped member 26 of FIG. 1, electrically-insulated 64, which in turn supports the active bare wire 66 at the end. In this case, the U 62 is in the plane of the side view of the electrode 60 and the active wire 66, still transverse to the longitudinal axis 68 of the electrode, also lies in the plane of the side view of the electrode, in contrast to the FIG. 1 embodiment in which the wire lies in a plane parallel to the top view of the electrode shown in that figure and in a plane perpendicular to the side view of the electrode shown in FIG. 3. In other words, the active wire 66 in FIG. 5 lies in a plane which is the same plane occupied by the plane of the U-shaped member 62 and that of the shaft 34 and shank 24, whereas the active wire 28 in FIGS. 1–3 lies in a plane which is the same plane occupied by the plane of the Y-shaped member 44 but angled 46 with respect to the plane of the shaft 34 and shank 24. The electrode shape of FIG. 5 is better suited for incisions on the anterior part of the nasal cartilage, and also offers the advantage of providing an improved view of the operative field. Preferred dimensions for this electrode are as follows: the horizontal part of the shaft 60 indicated at 72 is about 0.6–0.9 inches; the vertical part of the shaft 60 is about the same in length; the length of the U-shaped member 62, indicated at 74, is about 1.2–1.8 inches; the length of the active wire 66, indicated at 76, which happens to be approximately the same as the width (the vertical dimension in FIG. 5) of the U-shaped member 62, is about 0.1–0.2 inches. The length 74 of the U-shaped member 62 corresponds approximately to the length of the nose cartilage to be shaved off. Thus, it would be useful to have available a family of several electrodes with the configuration of FIG. 5 but with different U lengths 74 and different wire lengths 76 for removing different lengths of nose cartilage.

The insulating coatings 30 and 34 are essential to prevent accidental burning or other tissue damage by the sides of the electrode as the instrument is manipulated within the nasal cavity of the patient.

With the Ellman equipment, the fully rectified or cut/coag current is used at a power setting of about 3–4 with the active bare wire electrode 28. There is very little trauma and the sore area felt by the patient at the treated site is easily handled by analgesia and anti-inflammatory drugs.

Figure 6:
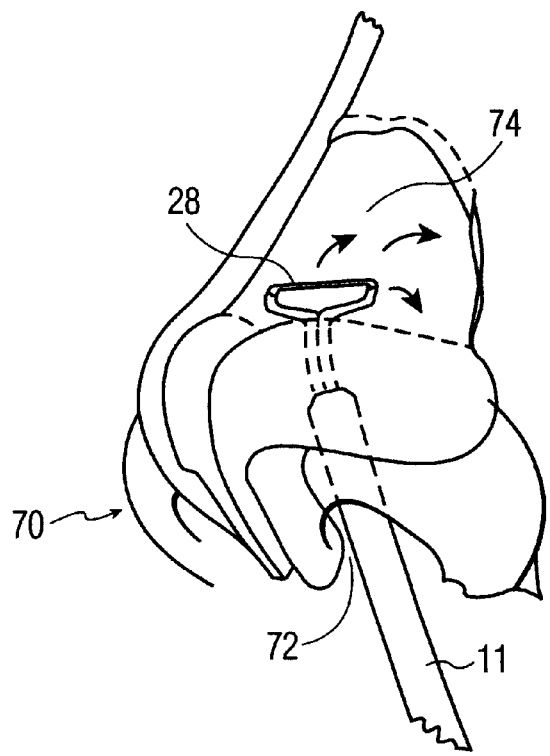
FIG. 6 is a perspective, schematic view illustrating how one of the electrodes of the invention can access the nasal cavity.
Figure 7:
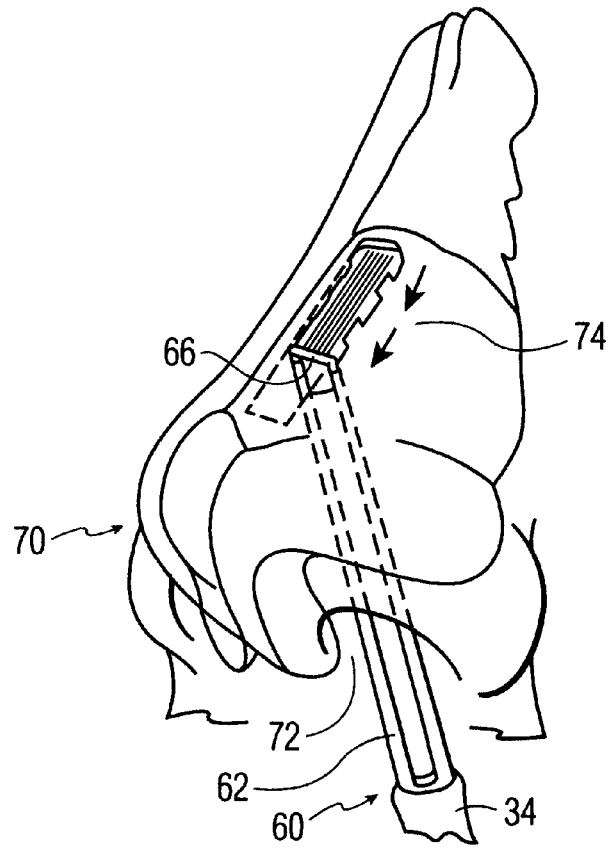
FIG. 7 is a perspective, schematic view illustrating how another one of the electrodes of the invention can access the nasal cavity.

FIGS. 6 and 7 illustrate how the unique shape and dimensions of the electrodes of the invention allow easy access to the nasal cavity. The nose is depicted at 70, and one of its nostrils at 72. In FIGS. 6 and 7, reference numeral 74 represents the cartilaginous dorsum. In the FIG. 6 view, the electrode 11 of FIG. 1 has been inserted into the nasal cavity via a nostril and is being used to reconfigure cartilage, as shown by the arrows, in elevation by the electrode of the overlying skin subcutaneous tissue canopy, the configuration of the electrode allowing it to remain in the favorable tissue plane intimate to the cartilaginous dorsum. In the FIG. 7 view, the electrode 60 of FIG. 5 has been inserted into the nasal cavity via a nostril and is being used, as shown by the arrows, for reduction of the cartilaginous dorsur, in elevation by the electrode of the periosteum overlying nasal bones, the long thin narrow configuration of the electrode being just sufficient to gain access to any existing nasal hump. It will be understood that a family of the electrodes differently configured as taught in the invention allows easy access and treatment of other nasal disorders and other nasal shapes and sizes.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A unipolar electrosurgical electrode for performing a rhinoplasty medical procedure, comprising:
    (a) an electrically-conductive shaft member having a first end for mounting to a handpiece and a second end, said first end having a longitudinal direction,
    (b) said second end comprising a generally Y-shaped or U-shaped wire-supporting portion extending in the longitudinal direction and terminated at its ends by an unbent thin straight active wire portion extending transverse to the longitudinal direction,
    (c) said transverse active wire portion being exposed electrically over its full length for applying electrosurgical currents to nasal cartilage tissue when said shaft member is connected to a source of electrosurgical currents,
    (d) the Y-shaped or U-shaped wire-supporting portions extending up to the transverse exposed wire portion being electrically-insulating to prevent contact and passage of electrosurgical currents to areas adjacent to or surrounding the tissue to be treated.

2. An electrosurgical electrode as claimed in claim 1, wherein the active wire portion has a length in its transverse direction of about 0.380–0.445 inches.

3. An electrosurgical electrode as claimed in claim 2, wherein the wire-supporting portion is Y-shaped and the active wire portion extends in a plane which is the same plane occupied by the plane of the Y-shaped member but angled with respect to the longitudinal direction.

4. An electrosurgical electrode as claimed in claim 1, wherein the wire-supporting portion is U-shaped and the active wire portion lies in a plane which is the same plane occupied by the plane of the U-shaped member and that of the first end.

5. An electrosurgical electrode as claimed in claim 2, wherein the active wire portion has a length in its transverse direction of about 0.1–0.2 inches.

6. An electrosurgical electrode as claimed in claim 5, wherein the active wire portion is constituted of a thin wire having a diameter of about 0.004–0.007 inches.

7. An electrosurgical electrode as claimed in claim 6, wherein the electrical insulation of the wire supporting portion is constituted by a coating having a thickness in the range of about 0.002–0.008 inches.

8. An electrosurgical electrode as claimed in claim 1, wherein the wire-supporting portion is Y-shaped and is angled downward with respect to the longitudinal direction at an angle of about 40–50°.

9. An electrosurgical electrode as claimed in claim 1, wherein the wire-supporting portion is Y-shaped and is angled upward with respect to the longitudinal direction at an angle of about 80–95°.

10. An electrosurgical electrode as claimed in claim 1, wherein the wire-supporting portion is U-shaped and is angled upward with respect to the longitudinal direction at an angle of about 80–95°.

11. An electrosurgical electrode as claimed in claim 1, wherein the wire-supporting portion is Y-shaped and its length is about 0.1–0.2 inches.

12. An electrosurgical electrode as claimed in claim 1, wherein the wire-supporting portion is U-shaped and its length is about 1.2–1.8 inches.

13. A rhinoplasty surgical procedure for a patient, comprising the steps:
    (a) providing electrosurgical apparatus connected to a handpiece holding a unipolar electrosurgical electrode, said electrosurgical electrode comprising:
        (i) an electrically-conductive shaft member having a first end for mounting to a handpiece and a second end, said first end having a longitudinal direction,
        (ii) said second end comprising a generally Y-shaped or U-shaped wire-supporting portion extending generally in the longitudinal direction and terminated at its ends by an unbent thin straight active wire portion extending transverse to the longitudinal direction, (iii) said transverse active wire portion being exposed electrically over its full length for applying electrosurgical currents to nasal cartilage tissue when said shaft member is connected to a source of electrosurgical currents, (iv) the Y-shaped or U-shaped wire-supporting portions extending up to the transverse exposed wire portion being electrically-insulating to prevent contact and passage of electrosurgical currents to areas adjacent to or surrounding the tissue to be treated, (b) placing the second end of the electrode inside of the nasal cavity of the patient and applying the active wire portion of the electrode to cartilage tissue within the nasal cavity of the patient and activating the electrosurgical apparatus, (c) moving the active wire portion of the electrode over the cartilage tissue within the nasal cavity of the patient to remove cartilage tissue.

14. A rhinoplasty surgical procedure as claimed in claim 12, wherein the wire-supporting portions are offset with respect to the first end of the electrode.

* * * * *